United States Patent
Waelde et al.

(10) Patent No.: US 10,374,284 B2
(45) Date of Patent: Aug. 6, 2019

(54) TOPOLOGY DETERMINATION OF A FILLING MATERIAL SURFACE WITH UNIFORM LINE SCANNING

(71) Applicant: VEGA GRIESHABER KG, Wolfach (DE)

(72) Inventors: Steffen Waelde, Niedereschach (DE); Roland Welle, Hausach (DE); Karl Griessbaum, Muehlenbach (DE); Josef Fehrenbach, Haslach (DE)

(73) Assignee: VEGA GRIESHABER KG, Wolfach (DE)

(*) Notice: Subject to any disclaimer, the term of this patent is extended or adjusted under 35 U.S.C. 154(b) by 83 days.

(21) Appl. No.: 15/510,003

(22) PCT Filed: Oct. 22, 2014

(86) PCT No.: PCT/EP2014/072685
§ 371 (c)(1),
(2) Date: Mar. 9, 2017

(87) PCT Pub. No.: WO2016/062341
PCT Pub. Date: Apr. 28, 2016

(65) Prior Publication Data
US 2017/0309989 A1 Oct. 26, 2017

(51) Int. Cl.
*H01Q 1/22* (2006.01)
*G01F 23/284* (2006.01)
(Continued)

(52) U.S. Cl.
CPC ............ *H01Q 1/225* (2013.01); *G01F 22/00* (2013.01); *G01F 23/284* (2013.01); *G01G 9/005* (2013.01); *G01N 11/00* (2013.01); *G01S 13/88* (2013.01); *H01Q 3/08* (2013.01); *H01Q 3/10* (2013.01); *H01Q 21/06* (2013.01)

(58) Field of Classification Search
CPC ............ H01Q 1/225; H01Q 3/08; H01Q 3/10; H01Q 21/06; G01F 22/00; G01F 23/284; G01G 9/005; G01N 11/00; G01S 13/88
(Continued)

(56) References Cited

U.S. PATENT DOCUMENTS

2004/0108951 A1 6/2004 Edvardsson
2006/0201246 A1 9/2006 Rolfes et al.
(Continued)

FOREIGN PATENT DOCUMENTS

DE 10 2004 041 857 A1 3/2006
DE 102004041857 A1 * 3/2006 ............ G01F 23/284
(Continued)

OTHER PUBLICATIONS

International Search Report dated Jul. 2, 2015 in PCT/EP2014/072685 filed Oct. 22, 2014.

*Primary Examiner* — Marrit Eyassu
(74) *Attorney, Agent, or Firm* — Oblon, McClelland, Maier & Neustadt, L.L.P.

(57) ABSTRACT

A fill level measurement device for determining a topology of a filling material surface is provided, including an antenna apparatus including an array of radiator elements and a rotatable mount configured to rotate the antenna apparatus about an axis that is in parallel with the array, such that a plurality of emission angles of the antenna apparatus are electronically and mechanically settable relative to the filling material surface without local overscanning occurring.

11 Claims, 4 Drawing Sheets

(51) Int. Cl.
*G01S 13/88* (2006.01)
*H01Q 3/08* (2006.01)
*H01Q 21/06* (2006.01)
*G01F 22/00* (2006.01)
*G01G 9/00* (2006.01)
*G01N 11/00* (2006.01)
*H01Q 3/10* (2006.01)

(58) Field of Classification Search
USPC .......................................................... 73/54.01
See application file for complete search history.

(56) References Cited

U.S. PATENT DOCUMENTS

| | | | |
|---|---|---|---|
| 2009/0299662 A1 | 12/2009 | Fehrenbach et al. | |
| 2010/0019952 A1* | 1/2010 | Poussin | B01J 8/0015 342/124 |
| 2012/0221261 A1* | 8/2012 | Fehrenbach | G01F 23/28 702/55 |
| 2013/0154846 A1* | 6/2013 | Mangione | G01V 3/12 340/854.6 |

FOREIGN PATENT DOCUMENTS

| | | | | |
|---|---|---|---|---|
| DE | 10 2007 012 938 A1 | 9/2008 | | |
| DE | 102007012938 A1 * | 9/2008 | | G01D 11/24 |
| EP | 1 701 142 A2 | 9/2006 | | |
| EP | 2 128 576 A1 | 12/2009 | | |
| WO | 2013/036727 A2 | 3/2013 | | |
| WO | WO 2013036727 A2 * | 3/2013 | | G01S 13/426 |

* cited by examiner

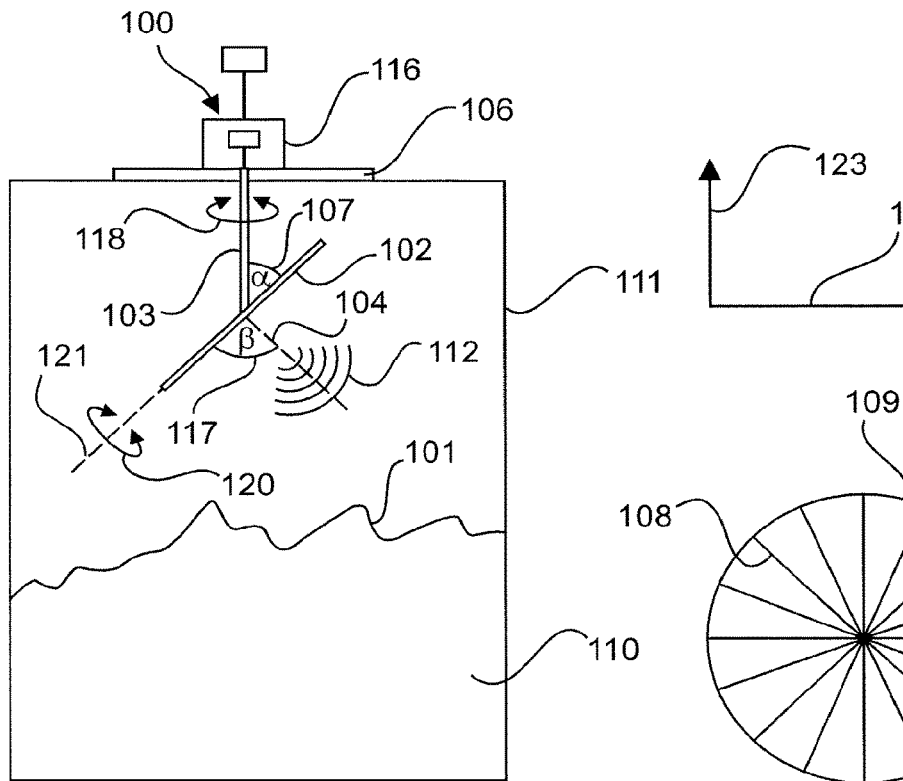
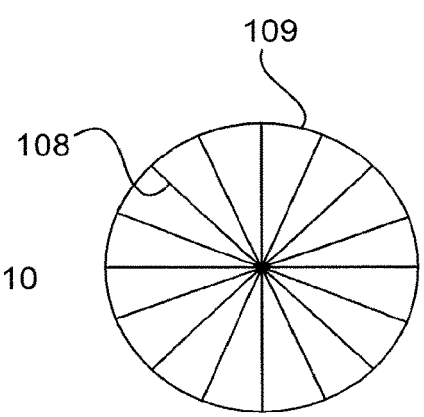
Fig. 1A
Fig. 1B
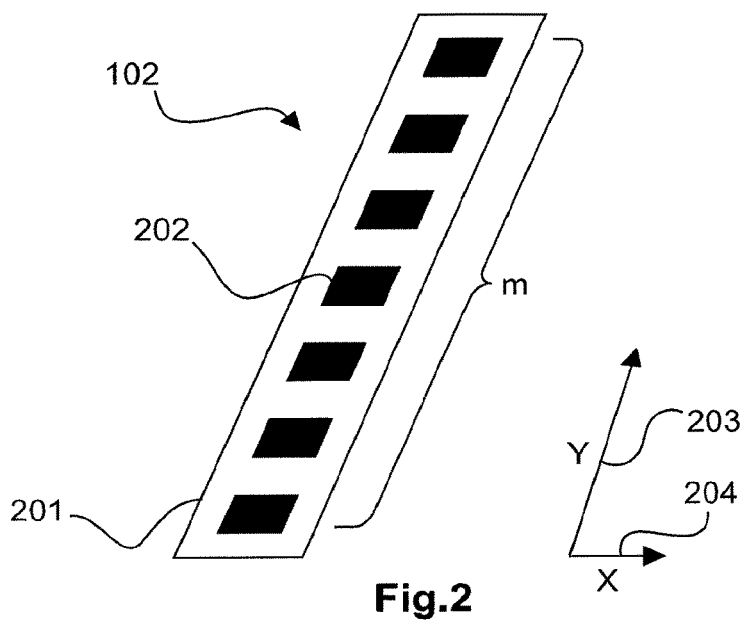
Fig. 2

TOPOLOGY DETERMINATION OF A FILLING MATERIAL SURFACE WITH UNIFORM LINE SCANNING

FIELD OF THE INVENTION

The invention relates to fill level measurement devices and to determining fill levels and filling material surface topologies. The invention also relates to measurement devices for object monitoring or mass flow determination. Furthermore, the invention relates to a method for determining a topology of a filling material surface and to the use of a fill level measurement device for determining a viscosity of a moving liquid and for determining the mass or volume of a medium.

BACKGROUND OF THE INVENTION

Recording the topology of a filling material surface may be advantageous in particular when measuring bulk materials and the resultant pouring cones or removal piles either inside or outside closed containers. It is also possible to record the topology of moving liquids. This changes for example when using stirrers and the flows associated therewith on the liquid surface, as a result of which so-called tornados may be produced. The topology can allow conclusions to be drawn about additional variables that are of interest, for example the viscosity or mixing of the filling medium. Here, the speed of the agitator may be taken into account.

Methods for contactlessly scanning a surface can, for example, be based on the principle whereby a signal emitted towards the surface is reflected by this surface and a propagation time or signal strength of the reflected signal is evaluated. In order to record the topology of the filling material surface sufficiently accurately, it may be necessary to carry out several measurements in the direction of certain regions of the filling material surface, which can increase the complexity and cost of such measurement equipment or measurement methods.

In order to scan the filling material surface, steerable measurement equipment or electronic beam controllers may be used that make it possible to scan the filling material surface.

SUMMARY OF THE INVENTION

The problem addressed by the present invention can be considered that of determining the topology of a filling material surface as effectively as possible.

This problem is solved by the subject matter of the independent claims. Additional embodiments of the invention can be found in the dependent claims and the following description.

A first aspect of the invention relates to a fill level measurement device configured to determine a topology of a filling material surface. The fill level measurement device comprises an antenna apparatus and a rotatable mount for rotating the antenna apparatus about a (first) axis that is perpendicular to a main emission direction of the antenna. The antenna apparatus comprises an array of radiator elements, for example in the form of patches, which is designed to transmit and/or receive electromagnetic measurement signals in the direction of the filling material surface. The (rotational) axis about which the rotatable mount can rotate the antenna apparatus may for example be in parallel with the array (or at an angle thereto that is not equal to 90 degrees) and is in the plane of the array, for example. The axis is not vertical in any case.

The fill level measurement device is designed such that a plurality of emission angles and/or receiving angles of the antenna apparatus can be set relative to the filling material surface both electronically and mechanically.

Therefore, the emission direction of the transmission signals can be changed by mechanically moving the antenna assembly in combination with electronically changing the antenna emission direction, for example by digital beam forming.

The rotatable mount and the electronic setting of emission angles and/or receiving angles of the antenna apparatus are coordinated with one another such that the antenna apparatus scans the filling material surface, or the bulk material surface in the case of bulk material, as uniformly as possible, for example line by line. In this way, overscanning of certain regions on the bulk material surface can be reduced or prevented entirely, and this means that the topology can be detected more rapidly.

Owing to the rotation of the antenna apparatus about the axis which is not perpendicular to the plane of the antenna apparatus in which the radiator elements are arranged and at the same time is not perpendicular to the filling material surface, line-by-line scanning of the bulk material surface can be carried out in combination with the electronic beam control without the scanning lines intersecting, since they are in parallel with one another.

In this context, it should be noted that the emission angle and/or receiving angle of the antenna apparatus can be electronically set in analogue form, for example by using antenna arrays in conjunction with suitable phase shifter circuits or analogue switches, and in digital form, for example by means of antenna arrays in conjunction with digital calculations on the digitalised receiving curves or echo signals.

According to an embodiment of the invention, the array is a unidimensional array that extends in a longitudinal direction, the axis being in parallel with the longitudinal direction of the array.

According to another embodiment of the invention, the emission angle and/or receiving angle are electronically set using digital beam-forming processes.

According to another embodiment of the invention, the fill level measurement device comprises an additional rotatable mount for rotating the antenna apparatus about a (second) axis that is not in parallel with the first axis. For instance, the additional axis is a vertical axis.

Therefore, the antenna apparatus has two rotational degrees of freedom.

According to another embodiment of the invention, the antenna apparatus is inclined in its longitudinal extension relative to a horizontal direction when the fill level measurement device is fitted or installed in the container so as to detect the topology of the filling material surface (or the bulk material surface). Here, the longitudinal extension extends in the plane in which the radiator elements are arranged.

In other words, the angle between the longitudinal direction of the antenna apparatus and the horizontal direction is not equal to zero degrees.

According to another embodiment of the invention, the fill level measurement device comprises a power supply and communications interface for connecting the fill level measurement device to a line, in particular a two-wire line or four-wire line, by means of which interface the fill level measurement device can be supplied with the power required for the measurement operation and by means of which measured data can be transmitted to a remote control unit.

The antenna apparatus may be a patch antenna, for example, which combines a plurality of individual, small, combined radiators (known as patches). These patches may for example be arranged on a common support or arranged on the printed circuit board in the form of a metal layer.

The emission angle and/or receiving angle of the antenna apparatus can be understood as the angle that results from the current main emission direction of the antenna apparatus relative to the longitudinal extension of the antenna apparatus. The emission angle and/or receiving angle can thus be changed without mechanically moving or changing a position of the antenna apparatus in space. The emission angle can be electronically set for example by overlay effects (constructive and destructive interference) in combination with a phase shift. For receiving, the receiving direction can be changed by a phase shift of the individual receiving channels of an array antenna relative to one another by means of known algorithms of digital beam forming.

According to another aspect of the invention, a method for determining a topology of a filling material surface is specified in which a fill level measurement device is first provided. In a subsequent step, a first emission angle of an antenna apparatus of the fill level measurement device is electronically and mechanically set, the antenna apparatus comprising an array of radiator elements for transmitting and/or receiving electromagnetic transmission/receiving signals. An echo curve is then detected at the first emission angle, following which the antenna apparatus is rotated about an axis which is in parallel with the array. Another echo curve is then detected at the second emission angle.

The many echo curves detected in this way provide the data required for calculating the topology of the filling material/bulk material surface.

According to another aspect of the invention, the use of a fill level measurement device as described above and in the following for determining a viscosity of a moving liquid is specified.

According to another aspect of the invention, the use of a fill level measurement device as described above and in the following for determining the mass or volume of a medium is specified.

According to another aspect of the invention, the use of a measurement device as described above and in the following for object monitoring is specified.

In the following, embodiments of the invention are described in detail with reference to the accompanying drawings.

BRIEF DESCRIPTION OF THE DRAWINGS

FIG. 1A shows a fill level measurement device according to an embodiment of the invention that is installed in a container.

FIG. 1B shows a scan pattern that can be achieved by rotating the antenna apparatus about a vertical (second) axis and by means of electronic beam control.

FIG. 2 shows an example of a unidimensional array antenna.

DETAILED DESCRIPTION OF EMBODIMENTS

Figures 3A, 3B:
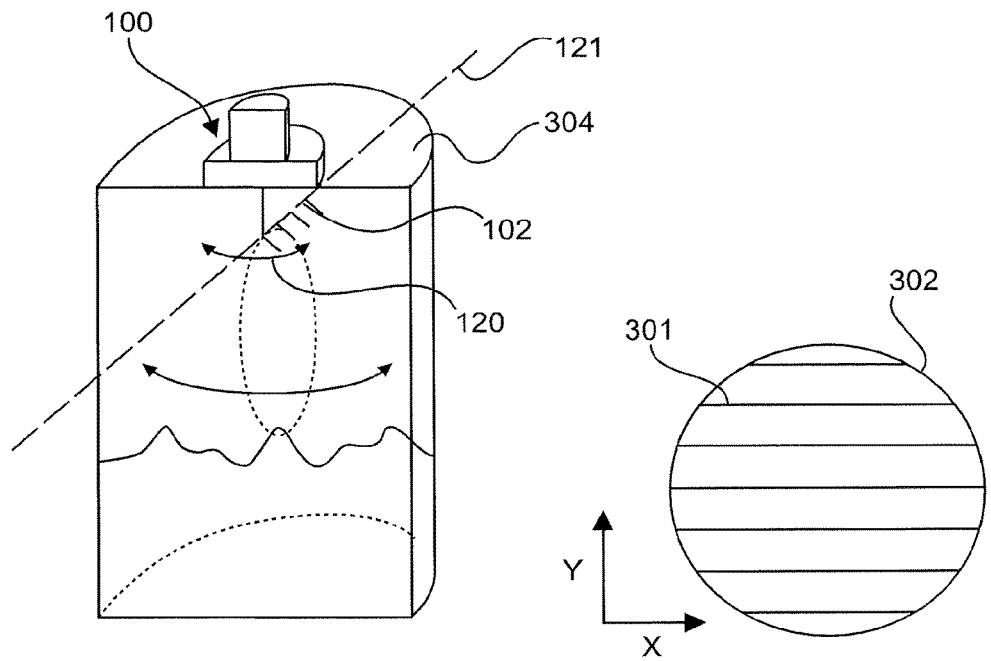
FIG. 3A shows a fill level measurement device in a container according to another embodiment of the invention.
FIG. 3B shows a scan pattern that can be achieved by rotating the antenna about an axis that is in parallel with the array of the antenna.

The views in the drawings are schematic and not to scale. When, in various figures, the same reference signs are used, they identify identical or corresponding elements. However, identical or corresponding elements may also be denoted by different reference signs.

FIG. 1 shows a fill level measurement device 100 for determining a topology of a surface 101 of a filling material or bulk material 110. The fill level measurement device 100 is attached to the container 111 and comprises an antenna apparatus 102 that can rotate about the axis 121 by means of a rotatable mount. This axis 121 is in parallel with the longitudinal extension of the antenna assembly 102. The rotational direction about the axis 121 is indicated by the arrow 120.

The antenna apparatus 102 is for example designed as a (unidimensional or two-dimensional) array antenna and has a main emission direction 104 that is typically perpendicular to the plane of the array. The emission direction 104 and in particular the angle β 117 formed between the emission direction 104 and the rotational axis 121 can be set by electronic beam control.

The antenna apparatus transmits an electromagnetic transmission signal 112, which is reflected by the filling material surface 101 and is radiated back to the antenna apparatus 102. The antenna apparatus receives the signal that is radiated back, and the high-frequency and electronics unit connected thereto forms an echo curve therefrom.

The fill level measurement device comprises an additional rotatable mount 103, by means of which the antenna apparatus 102 is connected to the main body 116 of the fill level measurement device and by means of which the antenna apparatus 102 can be rotated about the vertical axis, as indicated by the arrow 118.

The direction of the vertical axis is denoted by reference numeral 123 and the horizontal direction by reference numeral 122.

The fill level measurement device makes it possible to carry out a rapid and comparatively cost-effective method for detecting a topology of the filling material surface 101, since the main emission direction 104 of the fill level measurement device 100 is not changed purely mechanically or purely electronically, but instead this is carried out by a combined mechanical and electronic change in direction. For example, an electronic line scanner (antenna apparatus 102) is used that can be steered mechanically about the vertical (second) rotational axis and also about the (first) rotational axis 121.

According to FIG. 2, the line scanner 102 consists of a transceiver unit 201, which may consist of m (m=2, 3, 4, etc.) transmitting and/or receiving antenna elements (also referred to as radiator elements or patches) 202 arranged beside one another in a line. In this case, the y axis 203 extends along the longitudinal extension of the antenna apparatus, and the x axis 204 extends perpendicularly thereto within the plane of the antenna apparatus.

By electronically processing the individual signals from the transceiver units, the antenna characteristics of this line can be digitally influenced such that the main receiving direction can be steered in one dimension. A line has a narrow antenna opening angle in the y direction of 3 degrees, for example. Appropriate methods for beam steering are known to a person skilled in the art and are described in detail in the technical literature under the keywords "antenna array" and "digital beam forming".

The unidimensional antenna 201 can achieve very effective focusing of the resulting antenna characteristics in the direction of the Y extension 203 by using the subsequent algorithms for digital beam forming.

The rotational axis on which the line scanner is positioned extends in the vertical direction, i.e. in parallel with the surface normal of the container cover 106 (cf. FIG. 1A). The line scanner, which is attached to the rotatable shaft 103 at an angle 107, for example 45 degrees to the container cover, can scan a line 108 of the filling material surface 101 from the cross section of the container 109 by means of mechanical rotation and electronic beam forming (cf. FIG. 1B). In addition to a round cross section, the container may also have a polygonal cross section, or may be any other shape.

Using this angular position, a scanning pattern according to FIG. 1B is achieved. However, this pattern has the drawback that the scanning density depends on the distance from the centre. While the scanning density is highest in the centre, the density of scanned points decreases towards the edge.

FIG. 3A shows an antenna apparatus 102 arranged such that it can be used as a line scanner. Here, the individual antenna elements may be in a wide range of forms. For example, the antenna apparatus may be constructed as an array formed by horn radiators, patch antennas or planar Yagi antennas.

Alternatively or in addition to the vertical rotary shaft 103, as shown in FIG. 1A, a rotational axis 121 is provided that is arranged in parallel with the plane of the antenna assembly 102. In this way, a different scan pattern can be achieved, for example that which is shown in FIG. 3B, or a combination of the scan patterns from FIGS. 1B and 3B.

By combining mechanical and electronic beam steering, a topology can be detected in a cost-effective and time-optimised manner. Unevenly distributed point scanning can be prevented by a rotatably mounted axis 121 that is not in parallel with the surface normal of the container cover, but is preferably perpendicular thereto (cf. FIG. 3A) or, as in the embodiment in FIG. 1A, inclined relative thereto. For example, this axis extends in parallel with the longitudinal extension 203 of the array antenna (see FIG. 2).

Here, the antenna line can scan a pattern, as shown in FIG. 3B, by means of a clockwise and anticlockwise movement. In this case, the mechanical steering of the line scanner is carried out in the y direction and the electronic steering in the x direction. The individual scan lines 301 thus no longer have any points of intersection and result in a scan pattern having parallel lines in the cross section 302 of the container, and this leads to a shorter scanning time for topology detection.

Another possibility involves continuously rotating the antenna apparatus 102 about the axis 121. An advantage of the constant and uniform rotation is a lower mechanical load on the steered components.

Figures 4A, 4B:
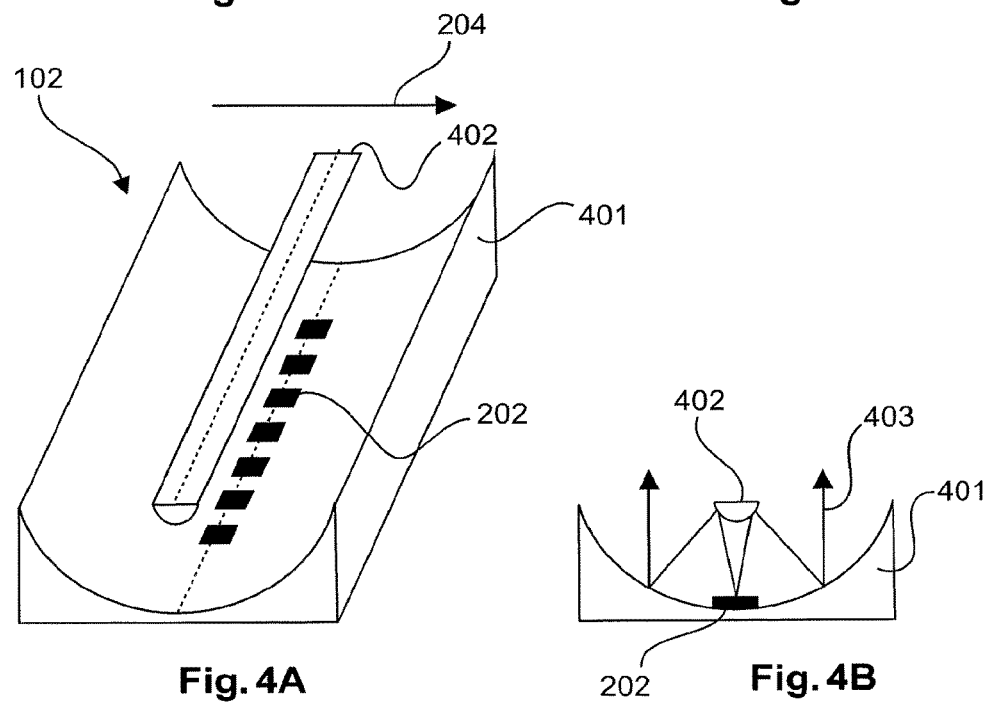
FIG. 4A shows a unidimensional array antenna according to an embodiment of the invention comprising a parabolic trough as the main reflector and a hyperbolically formed counter reflector.
FIG. 4B is a side view of the antenna from FIG. 4A.

FIGS. 4A and 4B show another embodiment of an antenna apparatus 102, of which the line scanner consists of a parabolic trough 401 as the main reflector and a hyperbolic rail 402 as the counter reflector. The individual antenna elements 202 are formed by horn radiators, patch antennas or Yagi antennas, for example. The parabolic trough improves the focus of the antenna characteristics in the x direction 204, and this can lead to a higher local resolution of the scanned topology.

In this case, the transmission signal 403 is emitted by the antenna elements 202 in the direction of the counter reflector 402 and is reflected thereby, and is then reflected again by the surface of the parabolic trough 401.

Figure 5A:
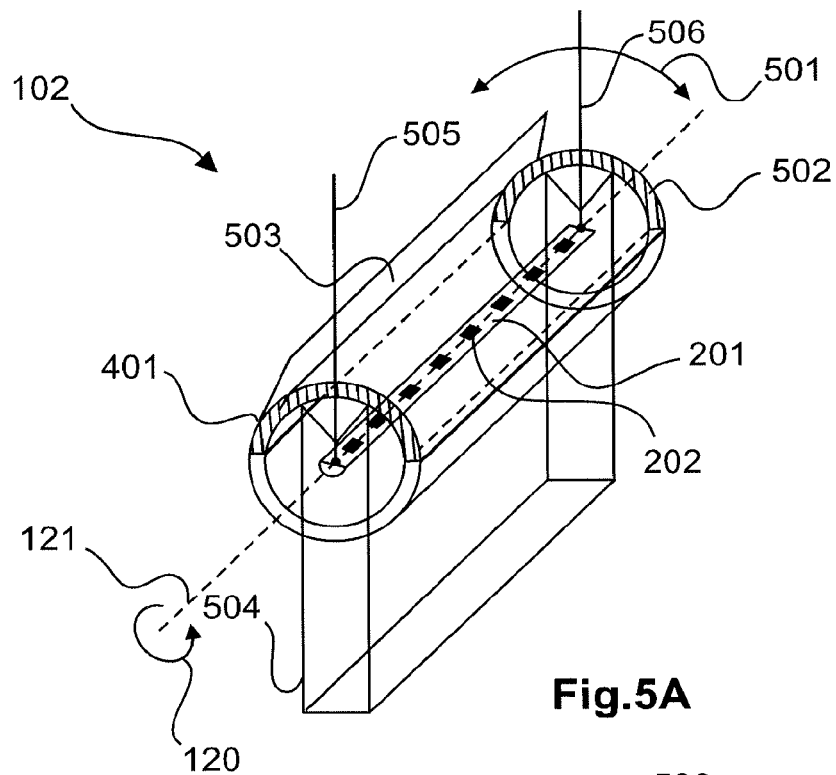
FIG. 5A shows an antenna apparatus according to an embodiment of the invention.
Figure 5B:
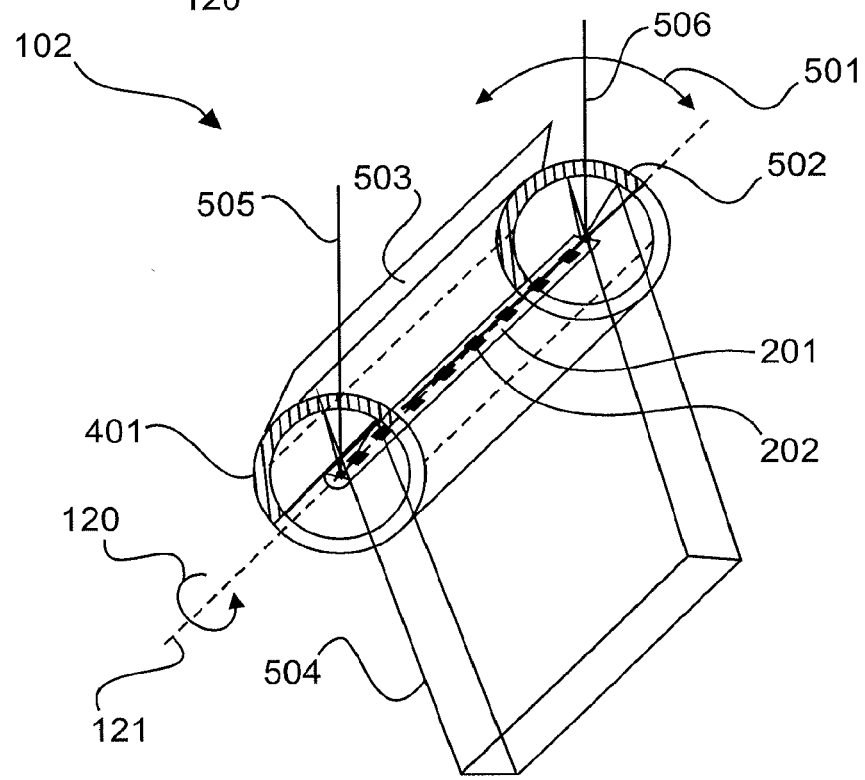
FIG. 5B shows the antenna apparatus from FIG. 5A after the antenna apparatus has rotated about the (first) axis.

The parabolic trough 401 may also be designed without a counter reflector 402, the power-supply elements 202 being positioned in the focal point of the parabolic trough in this case and the parabolic trough rotating about the power-supply elements, as shown in FIGS. 5A and 5B by the arrow 501. In this embodiment, the inner surface is parabolically formed and coated with metal in the region of the shaded area of the trough 401. The outer cross section may be circular, however. Advantageously, the steered components do not contain electrical components, and this means that the number of sliding contacts that are susceptible to wear can be reduced.

In order to protect against dust and deposit build-up, a radome 502 in the form of a cylindrical roller can be used that surrounds the respective antenna elements and is connected to the mechanically rotated components. A piece of mechanical equipment 503 may be provided, for example in the form of a plate or brush, which is used to remove deposit build-ups from the radome. The radome is transparent to the emitted and received high-frequency energy 504.

The antenna apparatus 102 is fastened to the housing of the fill level measurement device by means of two suspension means 505, 506. The two suspension means do not have to be in parallel.

FIG. 5B shows the antenna apparatus from FIG. 5A, with the parabolic trough being rotated anticlockwise by approximately 20 degrees.

Figure 6:
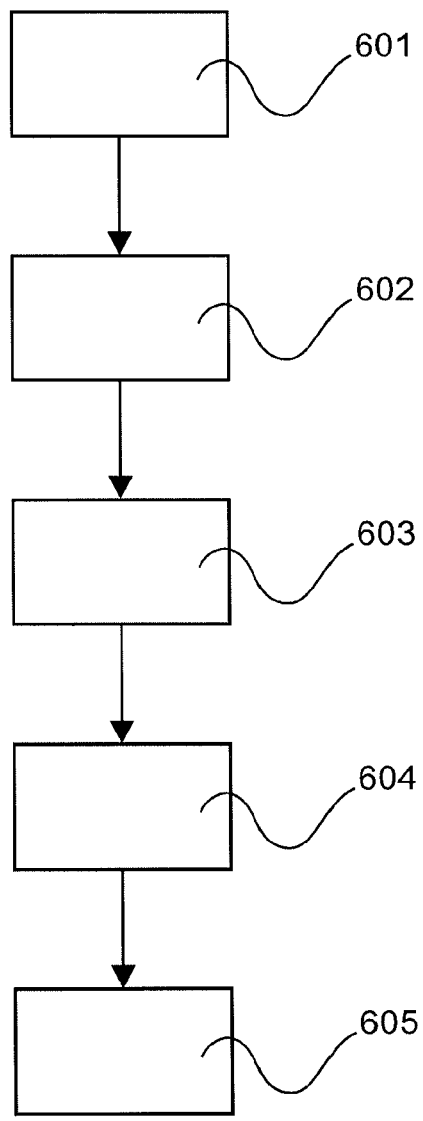
FIG. 6 shows a flow diagram of a method according to an embodiment of the invention.

FIG. 6 is a flow diagram of a method according to an embodiment of the invention. In step 601, a fill level measurement device is provided that is fastened to a container. In step 602, a first emission angle of an antenna apparatus of the fill level measurement device is electronically and mechanically set, following which an echo curve is detected at the first emission angle in step 603. In step 604, the antenna apparatus is then rotated about an axis which is in parallel with the array of the antenna apparatus. In step 605, another echo curve is recorded at a second emission angle. The topology of the filling material surface can be determined from echo curves of this type that are recorded at different emission angles.

It should additionally be pointed out that "comprising" does not exclude the possibility of further elements or steps, and "a", "an" or "one" does not exclude the possibility of a plurality. It should further be noted that features or steps which have been described with reference to one of the above embodiments may also be used in combination with other features or steps of other above-described embodiments. Reference signs in the claims shall not be deemed to have a limiting effect.

The invention claimed is:

1. A fill level measurement device for determining a topology of a filling material surface, comprising:
   an antenna apparatus comprising an array of radiator elements configured to transmit and/or receive electromagnetic signals, wherein the array is a unidimensional array that extends in a longitudinal direction; and a first rotatable mount configured to rotate the antenna apparatus about a non-vertical axis, wherein the non-vertical axis is in parallel with the longitudinal direction, wherein the device is configured to electronically and mechanically set a plurality of emission angles and/or receiving angles of the antenna apparatus relative to the filling material surface in order to scan the filling material surface line-by-line.

2. The fill level measurement device according to claim 1, wherein the non-vertical axis is in parallel with the array.

3. The fill level measurement device according to claim 1, wherein the device is further configured to set the plurality of emission angles and/or receiving angles electronically by digital beam-forming processes.

4. The till level measurement device according to claim 1, wherein the device is further configured to set the plurality of emission angles and/or receiving angles electronically by analogue phase shifters and/or by analogue switches.

5. The fill level measurement device according to claim 1, further comprising an additional rotatable mount configured to rotate the antenna apparatus about a shaft that is not in parallel with the array.

6. The till level measurement device according to claim 5, wherein the additional shaft is a vertical shaft.

7. The till level measurement device according to claim 1, wherein the antenna apparatus is inclined in a longitudinal extension direction thereof relative to a horizontal direction, such that an angle between the longitudinal extension direction of the antenna apparatus and the horizontal direction is not equal to 0°.

8. The fill level measurement device according to claim 1, further comprising a power supply and a communications interface configured to connect the fill level measurement device to a two-wire line, by which interface the fill level measurement device is supplied with power for measurement operation and by which measured data is transmittable to a remote control unit.

9. A method for determining a topology of a filling material surface, comprising:
providing a fill level measurement device;
electronically and mechanically setting a first emission angle of an antenna apparatus of the fill level measurement device, the antenna apparatus comprising an array of radiator elements configured to transmit and/or receive electromagnetic signals, wherein the array is a unidimensional array that extends in a longitudinal direction;
detecting an echo curve at the first emission angle;
rotating the antenna apparatus about a non-vertical axis in parallel with the array, wherein the non-vertical axis is in parallel with the longitudinal direction;
detecting another echo curve at a second emission angle; and
determining the topology of the filling material surface by scanning the filling material surface line-by-line.

10. The method according to claim 9, further comprising determining, by the fill level measurement device, a viscosity of a moving liquid.

11. The method according to claim 9, further comprising determining, by the fill level measurement device, a mass or a volume of a medium.

* * * * *